(12) United States Patent
Nozawa et al.

(10) Patent No.: US 6,696,034 B2
(45) Date of Patent: Feb. 24, 2004

(54) METHOD FOR PRODUCING HYDROPHOBIC SILICA FINE POWDER

(75) Inventors: Yasuaki Nozawa, Annaka (JP); Kiyoshi Shirasuna, Annaka (JP); Hidekazu Uehara, Annaka (JP); Keiji Shibata, Annaka (JP); Susumu Ueno, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 337 days.

(21) Appl. No.: 09/941,727

(22) Filed: Aug. 30, 2001

(65) Prior Publication Data

US 2002/0025288 A1 Feb. 28, 2002

(30) Foreign Application Priority Data

Aug. 31, 2000 (JP) ..................... 2000-262227

(51) Int. Cl.[7] .................. C09C 1/30; C01B 33/12
(52) U.S. Cl. ......................... 423/336; 423/337
(58) Field of Search ................. 423/335, 336, 423/337; 106/490, 491

(56) References Cited

U.S. PATENT DOCUMENTS 4,503,092 A    3/1985  Klebe et al. ............. 423/336
4,554,147 A  * 11/1985  Stoll et al. ............... 423/337
5,342,597 A  *  8/1994  Tunison, III ............. 423/336
5,372,795 A  * 12/1994  Muhlhofer et al. ....... 423/337
5,902,636 A  *  5/1999  Grabbe et al. ............ 423/336
5,919,298 A  *  7/1999  Griffith et al. ........... 423/337

FOREIGN PATENT DOCUMENTS

DE    1163784       2/1964
DE    A1-3211431    9/1983
JP    A6-206720     7/1994

* cited by examiner

Primary Examiner—Ngoc-Yen Nguyen
(74) Attorney, Agent, or Firm—Birch, Stewart, Kolasch & Birch, LLP

(57) ABSTRACT

Hydrophobic silica fine powder is produced by pyrolyzing a silane compound to form a silica fine powder and hydrophobizing the silica fine powder with an organohalosilane as hydrophobizing agent in a fluidization vessel. A portion of the silica fine powder is bypassed to a waste gas line from the fluidization vessel and collected with a cyclone and bag filter, and the collected powder is fed to the fluidization vessel where it is hydrophobized. The amount of unreacted organohalosilane in the waste gases is reduced, alleviating the burden on waste gas treatment. The silica having the unreacted organohalosilane borne thereon is fed back to the fluidization vessel, increasing the reaction efficiency of organohalosilane.

2 Claims, 1 Drawing Sheet

METHOD FOR PRODUCING HYDROPHOBIC SILICA FINE POWDER

BACKGROUND OF THE INVENTION

1. Field of the Invention

The present invention relates to a method for producing hydrophobic silica fine powder which can be used as a thickener for coatings, adhesives and synthetic resins, as a reinforcement for plastics, and to improve flowability in toners for copiers.

2. Prior Art

West German Patent No. 1163784 discloses that pyrogenic silica (silicon dioxide) having silanol groups on the surface is hydrophobized with dimethyldichlorosilane as a hydrophobizing agent in a parallel flow fluidized bed at 400 to 600° C. in the presence of steam while feeding nitrogen for fluidization. This process is uneconomical since a substantial amount of unreacted silane hydrophobizing agent is carried over with the waste gases. West German Patent P3211431.1 describes that waste gases resulting from hydrophobizing reaction are fed back to the hydrophobizing process whereby unreacted silane is also fed back to the hydrophobizing process, which enables to reduce the amount of silane hydrophobizing agent used. This method, however, is complex and requires to control the flow rate and pressure of waste gases. JP-A 6-206720 (U.S. Pat. No. 5,372,795) discloses that waste gases containing unreacted silane are recycled to a combustion chamber where they are burned. This method also requires to control the flow rate of waste gases since combustion fluctuates unless the amounts of air/hydrogen/starting silane and waste gases are controlled as appropriate.

In a process of hydrophobizing silica fine powder in a fluidization vessel, the silica is often treated with an organohalosilane (referred to simply as "silane," hereinafter), typically dimethyldichlorosilane as hydrophobizing agent. The resulting waste gases contain a noticeable amount of unreacted silane hydrophobizing agent. The presence of silane in the waste gases leads to a number of practical obstacles when the silane-containing waste gases are treated with a scrubber, such as the formation of foam, which cannot be easily removed with filters.

SUMMARY OF THE INVENTION

An object of the invention is to provide a method for producing hydrophobic silica fine powder at an improved reaction efficiency of hydrophobizing agent and a reduced burden on waste gas treatment.

The invention concerns to a method for producing hydrophobic silica fine powder by pyrolyzing a silane compound to form a silica fine powder and hydrophobizing the silica fine powder with an organohalosilane in a fluidization vessel. In studies to reduce the amount of unreacted silane in waste gases without complicating the process and its control, we have found that by feeding a portion of silica resulting from flame hydrolysis to a waste gas line from the hydrophobizing step, contacting the silica with unreacted silane being carried over with the waste gases, and feeding the silica to the hydrophobizing step, the amount of unreacted silane in waste gases can be reduced, thereby alleviating the burden on waste gas treatment; and unreacted silane is fed back to the fluidization vessel along with the silica, thereby increasing the reaction efficiency of silane.

In an experiment, a cyclone and a bag filter were installed in the waste gas line to recover silica that had flown out from the fluidization vessel. On measuring the temperature at various places in the waste gas line, we have found that, if the temperature of the waste gas line is maintained at 100° C. or higher, the moisture present in the waste gases does not condense and undesirable products such as gels or oils due to moisture and unreacted silane do not form. In particular, the absence of gel or oil formation on the filter fabric in a bag filter keeps the filter fabric free of clogging, making it possible to carry out continuous operation. By maintaining the waste gases at 100° C. or higher, essentially 100% of fugitive silica in the waste gases can be recovered with the cyclone and bag filter. It has been found that the amount of unreacted silane in the waste gases can be reduced by feeding a portion of silica fine powder resulting from pyrolysis to the waste gas line, contacting the silica with unreacted silane, collecting the silica in the cyclone and bag filter, and feeding the collected silica to the fluidization vessel where it is hydrophobized. This is presumably because the unreacted silane is brought in effective contact with the silica upon collection of the silica with the cyclone and bag filter fabric.

Accordingly, the invention provides a method for producing hydrophobic silica fine powder. A silane compound is pyrolyzed to form a silica fine powder. The silica fine powder is then hydrophobized with an organohalosilane in a fluidization vessel. A portion, specifically 3 to 20% by weight of the silica fine powder is directly fed to a waste gas line from the fluidization vessel and collected with a cyclone and bag filter. The collected powder is fed to the fluidization vessel where it is hydrophobized. The cyclone and the bag filter are preferably held at a temperature of at least 100° C.

In the process involving flame hydrolysis of silane to form pyrogenic silica (silicon dioxide fine powder) and hydrophobizing the pyrogenic silica in a fluidization vessel with a hydrophobizing agent, the invention is to feed a portion of the pyrogenic silica to the waste gas line where the silica is contacted with the unreacted hydrophobizing agent carried over with the waste gases and then feed the silica to the fluidization vessel. As a result, the amount of unreacted hydrophobizing agent in the waste gases is reduced, whereby the burden on waste gas treatment is alleviated. Additionally, the unreacted hydrophobizing agent is fed back to the fluidization vessel along with the silica, whereby the reaction efficiency of hydrophobizing agent is increased.

BRIEF DESCRIPTION OF THE DRAWING

The objects, features and advantages of the invention will become more apparent from the following detailed description, taken in conjunction with the accompanying drawing.

The only FIGURE.

DETAILED DESCRIPTION OF THE INVENTION

Figure 1:
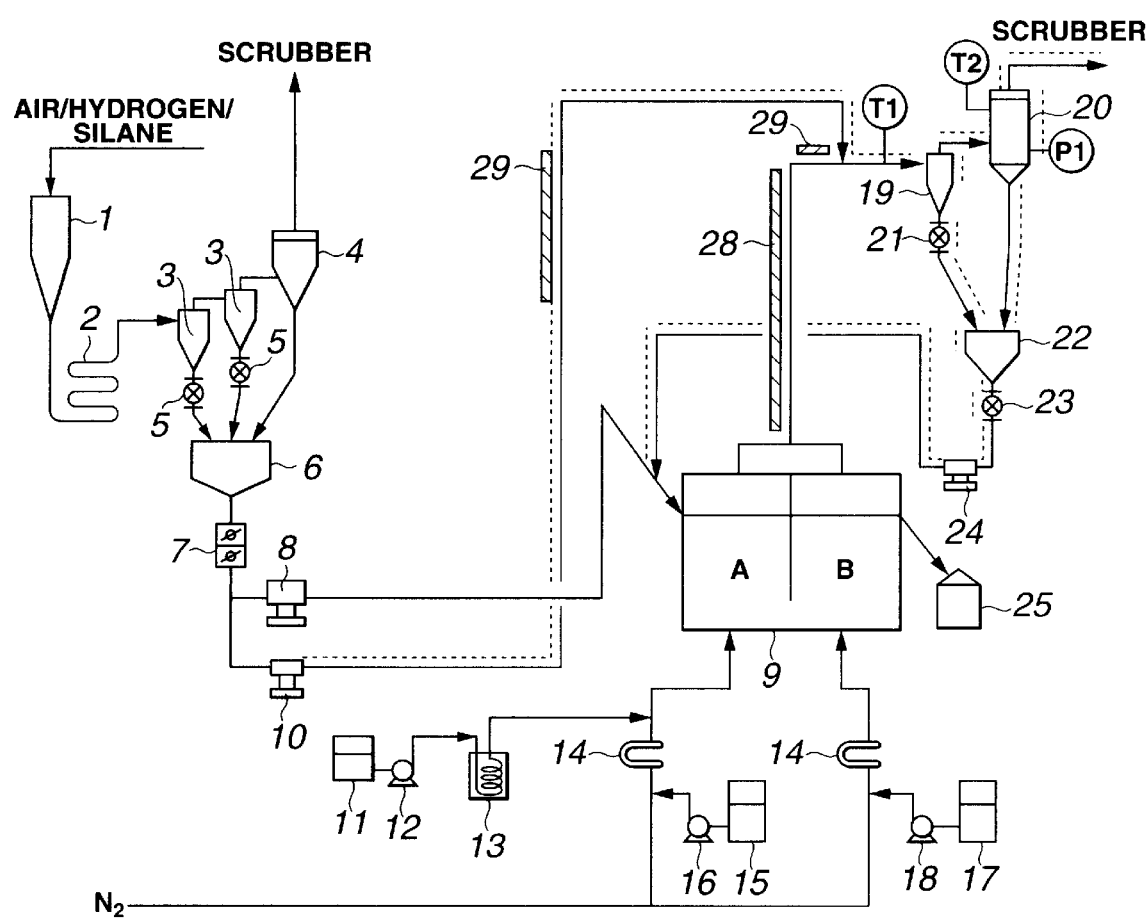
FIG. 1 is a flow diagram illustrating an embodiment of the invention.

The inventive process for producing hydrophobic silica fine powder involves pyrolyzing a silane compound (a halogenated silicon compound) to form a silicon dioxide fine powder (pyrogenic silica), then treating the pyrogenic silica in a fluidization vessel with a hydrophobizing agent, more specifically an organohalosilane.

The pyrogenic silica may be prepared by a known process using a halogenated silicon compound such as methyltrichlorosilane. A silica powder having a BET specific surface area of 50 to 400 m$^2$/g is desirable in terms of flow and other factors associated with the subsequent hydrophobizing step.

After pyrogenic silica is prepared by a known method from a halogenated silicon compound, it is preferably agglomerated and halogen gases such as chlorine are separated off and removed. Thereafter, the agglomerated silica is hydrophobized in a fluidization vessel using an organohalosilane as the hydrophobizing agent and using also steam and an inert gas. In a preferred embodiment, the fluidization vessel is divided into a hydrophobizing section and a deacidifying section. Hydrophobization of the pyrogenic silica is carried out in the hydrophobizing section, followed by deacidification in the deacidifying section.

According to the invention, a portion of the silica prior to the hydrophobizing step is fed to a waste gas line from the fluidization vessel which is terminally connected to a cyclone and a bag filter. The remainder of the silica is normally fed to the fluidization vessel (including hydrophobizing and deacidifying sections) where it is hydrophobized and deacidified. A part of the hydrophobized silica fine powder flies out of the fluidization vessel into the waste gas line and is collected with the cyclone and bag filter. The silica (including both non-hydrophobized and hydrophobized silicas) collected in the cyclone and bag filter is returned to the fluidization vessel, and especially the hydrophobizing section. In the deacidifying section, adding 0.1 to 1 vol % of water to the fluidizing gas is preferable for promoting flow.

In one preferred embodiment, production and recovery of hydrophobized silica fine powder is carried out as a continuous process within an apparatus that includes a pyrogenic silica-producing operation. However, this is not an essential feature of the invention.

Referring to FIG. 1, a preferred embodiment of the invention is described below. Pyrogenic silica is produced according to a conventional process by burning a halogenated silicon compound together with hydrogen and air in a combustion chamber (pyrolyzing means) 1 and agglomerated by an agglomerator (agglomerating means) 2 for subsequent collection by cyclones 3 and a bag filter 4. Use of the cyclones 3 and bag filter 4 also serves to separate off chlorine and other halogen-containing gases that form as by-products in the combustion chamber 1. The separated halogen-containing gases are sent to a scrubber. The agglomerated silica then passes through rotary valves 5 and is collected in a hopper 6. Agglomerated silica that has been retrieved by the bag filter 4 also is recovered in the hopper 6.

Next, the agglomerated silica passes through a double damper 7, and a majority thereof is delivered by a diaphragm pump 8 to a fluidization vessel 9 for hydrophobization. A portion of the agglomerated silica, specifically 3 to 20% by weight, and preferably 5 to 15% by weight of the agglomerated silica is delivered by another diaphragm pump 10 to a waste gas line extending from the fluidization vessel 9, for bringing the silica in contact with unreacted hydrophobizing agent (organohalosilane).

The fluidization vessel 9 is divided into a hydrophobizing section A and a deacidifying section B. In the apparatus depicted in FIG. 1, the hydrophobizing section A and the deacidifying section B communicate in the lower portion of the fluidization vessel 9. Silica hydrophobization is carried out in hydrophobizing section A, and the halogen gas such as chlorine which accompanies the silica from the hydrophobizing section A is removed in the deacidifying section B. Alternatively, hydrophobization and deacidification may be carried out in separate devices.

In the hydrophobizing section A, the silica is fluidized with an inert gas, generally nitrogen ($N_2$), and is treated with a hydrophobizing agent. In the apparatus shown in FIG. 1, the hydrophobizing agent 11 is sent by a pump 12 through a vaporizer 13 and to the fluidization vessel 9. The hydrophobizing agent 11 may be mixed with the silica before the silica enters the fluidization vessel 9. An alternative is to heat fluidizing nitrogen having water entrained thereon, then mix the hydrophobizing agent into the gas stream and introduce the resulting mixture into the fluidization vessel 9.

The silica is hydrophobized at a temperature of preferably 400 to 600° C., and most preferably 450 to 550° C. The flow velocity is preferably from 1 to 6 cm/s, although a velocity within a range of 1.4 to 3 cm/s is especially preferred for achieving a stable fluidized state and holding down the fly-out of silica. Water is used at this point because it has a beneficial effect on hydrophobizing treatment. The water 15 is fed with a pump 16 to the fluidizing inert gas, following which the gas is heated with a heater 14 and introduced to the hydrophobizing section A of the fluidization vessel 9. The amount of water used for hydrophobization is preferably 0.1 to 5 parts by weight, and most preferably 0.5 to 3 parts by weight, per 100 parts by weight of silica. The hydrophobizing agent is an organohalosilane, and most preferably dimethyldichlorosilane.

In the deacidifying section B, the silica is fluidized with an inert gas, typically nitrogen, and subjected to deacidification. Water is typically added to the fluidizing gas so that deacidification can be carried out in a humid atmosphere. Preferably, as shown in FIG. 1, the water 17 is added to the fluidizing gas with a pump 18, following which the gas is heated with a heater 14 and introduced to the deacidifying section B. The amount of water added to the fluidizing gas for this purpose is preferably at least 0.1 vol %, and most preferably 0.1 to 1 vol %. In the absence of moisture, the silica may become less flowable, making it necessary to use more fluidizing gas, which in turn results in increased fly-out. This is particularly undesirable from the standpoint of the burden on the bag filter. On the other hand, too much moisture may give rise to such undesirable effects as condensation when the deacidified silica is recovered in a recovery vessel 25 from the deacidifying section B.

The deacidification temperature is preferably 400 to 500° C., and the flow velocity is preferably 1 to 6 cm/s.

Waste gases from the fluidization vessel 9 (including both hydrophobizing section A and deacidifying section B) are discharged through the waste gas line and sent to a scrubber via a cyclone 19 and a bag filter 20. On the way to the cyclone 19, the waste gases merge with the bypass portion of non-hydrophobized silica. Silica accompanying the waste gases (including both fugitive hydrophobized silica from the fluidization vessel 9 and non-hydrophobized silica bypassed from the hopper 6) passes from the cyclone 19 to a rotary valve 21 or is trapped by the bag filter 20, then is collected in a hopper 22. The collected silica is then returned to the hydrophobizing section A via a rotary valve 23 and a diaphragm pump 24. The deacidified silica is collected in the recovery vessel 25.

Unreacted silane is present within the waste gases. The condensation of moisture within the waste gases on the walls of the apparatus at temperatures below 100° C. converts the silane into a gel or oil, which obstructs pipelines and in particular clogs the pores of the filter fabric used in the bag filter 20. Accordingly, it is necessary to maintain the interior of the waste gas line at a temperature of at least 100° C. In FIG. 1, T1 and T2 are each thermometers which measure the temperature of the waste gases. The temperature readings at T1 and T2 must be at least 100° C., although a higher temperature, such as 130° C. or more, is preferred for areas of the equipment that come into direct contact with the gases. The formation of gummy or oily deposits on the filter fabric of the bag filter 20 results in clogging and an increased pressure difference, making normal operation difficult. It is thus desirable to install a differential pressure gauge P1 on the bag filter 20 to monitor changes in the pressure difference. The production apparatus shown in FIG. 1 is also provided with a heat insulator 28 and a steam tracer 29 to keep the temperature from falling.

The properties of the hydrophobic silica produced by the method of the invention are not subject to any particular limitation, although a specific surface area of about 110 $m^2/g$, a carbon content of at least about 0.9 wt %, and a pH of at least 4.5 are preferred. Hydrophobic silica having such properties is highly suitable for use in sealants and related applications.

EXAMPLE

The following examples are provided to illustrate the invention, and are not intended to limit the scope thereof.

Example 1

In the apparatus shown in FIG. 1, 50.6 kg/h of methyltrichlorosilane was burned together with hydrogen and air, producing 20.2 kg/h of silica. A major portion (17.2 kg/h) of the silica was fed to the fluidization vessel 9 through the diaphragm pump 8, and the remainder (3.0 kg/h) of the silica was fed to the waste gas line through the diaphragm pump 10. The former silica was subjected to hydrophobizing treatment at a nitrogen feed rate of 30 $Nm^3/h$, a dimethyldichlorosilane feed rate of 1.6 kg/h, and a water feed rate of 0.5 kg/h into section A of the fluidization vessel 9, and a temperature of 490° C. The fluidization velocity of silica inside section A was about 2.0 cm/s. The hydrophobized silica was then deacidified at a nitrogen feed rate of 35 $Nm^3/h$ and a water feed rate of 0.2 kg/h to section B of the fluidization vessel 9, a temperature of 480° C., and a flow velocity of about 2.2 cm/s. The temperatures of the cyclone 19 and the bag filter 20 were 150° C. (T1) and 135° C. (T2). The treated silica had a specific surface area of 114 $m^2/g$, a carbon content of 1.02 wt %, and a pH of 4.7. It was determined from the carbon content of the treated silica that about 70% of dimethyldichlorosilane had reacted.

Under the above-described conditions, operation was continued for a total of 100 hours. Little or no clogging occurred in the line from the bag filter to the scrubber. Very little foaming of the waste gas scrubbing liquid was observed.

Comparative Example 1

In the apparatus shown in FIG. 1, 50.3 kg/h of methyltrichlorosilane was burned together with hydrogen and air, producing 20.0 kg/h of silica. The entirety of the silica was fed to the fluidization vessel 9 through the diaphragm pump 8. Otherwise, operation was the same as in Example 1. The treated silica had a specific surface area of 117 $m^2/g$, a carbon content of 0.85 wt %, and a pH of 4.7. It was determined from the carbon content that about 58% of dimethyldichlorosilane had reacted.

According to the invention, by bypassing a portion of silica resulting from hot hydrolysis to a waste gas line where unreacted organohalosilane is present, thereby contacting the silica with the unreacted organohalosilane, and feeding the silica to the fluidization vessel where it is treated again, the amount of unreacted organohalosilane in the waste gases is reduced, whereby the burden on waste gas treatment is alleviated. Additionally, the silica having contacted with the unreacted organohalosilane is fed back to the fluidization vessel, whereby the reaction efficiency of organohalosilane or hydrophobizing agent is increased.

Japanese Patent Application No. 2000-262227 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for producing hydrophobic silica fine powder, comprising the steps of pyrolyzing a silane compound to form a silica fine powder and hydrophobizing the silica fine powder with an organohalosilane in a fluidization vessel; wherein 3 to 20% by weight of the silica fine powder is directly fed to a waste gas line from said fluidization vessel and collected with a cyclone and bag filter, and the collected powder is fed to the fluidization vessel where it is hydrophobized.

2. The method of claim 1 wherein said cyclone and bag filter are held at a temperature of at least 100° C.

* * * * *